United States Patent
Rosielle et al.

(10) Patent No.: US 10,888,384 B2
(45) Date of Patent: Jan. 12, 2021

(54) SURGICAL ROBOT

(71) Applicant: Technische Universiteit Eindhoven, Eindhoven (NL)

(72) Inventors: Petrus Carolus Johannes Nicolaas Rosielle, Veldhoven (NL); Hildebert Christiaan Matthijs Meenink, Steenderen (NL)

(73) Assignee: Technische Universiteit Eindhoven, Eindhoven (NL)

( * ) Notice: Subject to any disclaimer, the term of this patent is extended or adjusted under 35 U.S.C. 154(b) by 206 days.

(21) Appl. No.: 15/236,755

(22) Filed: Aug. 15, 2016

(65) Prior Publication Data

US 2016/0346052 A1    Dec. 1, 2016

Related U.S. Application Data

(63) Continuation-in-part of application No. 13/971,300, filed on Aug. 20, 2013, now abandoned, which is a continuation-in-part of application No. 12/301,158, filed as application No. PCT/NL2007/000117 on May 4, 2007, now Pat. No. 8,512,353, said application No. 13/971,300 is a continuation-in-part of application No. 13/499,374, filed as application No. PCT/NL2010/050641 on Oct. 1, 2010, now Pat. No. 9,060,795.

(51) Int. Cl.
| | | |
|---|---|---|
| *A61B 34/30* | (2016.01) | |
| *A61D 1/00* | (2006.01) | |
| *A61F 9/007* | (2006.01) | |
| *A61B 34/37* | (2016.01) | |
| *A61B 17/00* | (2006.01) | |

(52) U.S. Cl.
CPC .............. *A61B 34/30* (2016.02); *A61B 34/37* (2016.02); *A61D 1/00* (2013.01); *A61F 9/007* (2013.01); *A61B 2017/00292* (2013.01); *A61B 2034/302* (2016.02); *A61B 2034/305* (2016.02); *Y10S 901/06* (2013.01)

(58) Field of Classification Search
CPC ......... A61F 9/007; A61D 1/00; Y10S 901/06; A61B 34/30; A61B 34/37; A61B 2034/305; A61B 2017/00292; A61B 2034/302; A61B 19/2203; A61B 2019/2223
USPC .............................................. 606/1, 130, 139
See application file for complete search history.

(56) References Cited

U.S. PATENT DOCUMENTS

| | | | | | |
|---|---|---|---|---|---|
| 4,445,893 | A | * | 5/1984 | Bodicky | ........... A61M 25/0606 604/165.04 |
| 5,257,998 | A | * | 11/1993 | Ota | ......... A61B 90/11 414/917 |

(Continued)

*Primary Examiner* — Amy R Weisburg
(74) *Attorney, Agent, or Firm* — Lumen Patent Firm

(57) ABSTRACT

A surgical robot for performing minimally invasive surgery (e.g. in the eye) is provided. A cannula connection is positioned at a fixed surgical arm part and aligned with a movable surgical arm part movable with respect to the fixed surgical arm part. A surgical instrument can be mounted at the movable part. The surgical instrument can pass through the cannula connection. Reference arm(s) and manipulation arm(s) connect a base element with the fixed surgical arm part. The base element could have a surgical operating table attachment part to movably attach to a surgical operating table and rotating parts movably attached to the surgical operating table attachment part.

7 Claims, 4 Drawing Sheets

(56) References Cited

U.S. PATENT DOCUMENTS

| | | | |
|---|---|---|---|
| 7,955,322 B2* | 6/2011 | Devengenzo | A61B 1/00149 |
| | | | 606/1 |
| 2003/0109825 A1 | 6/2003 | Loser | |
| 2016/0166344 A1* | 6/2016 | Prisco | B25J 9/1674 |
| | | | 606/130 |

* cited by examiner

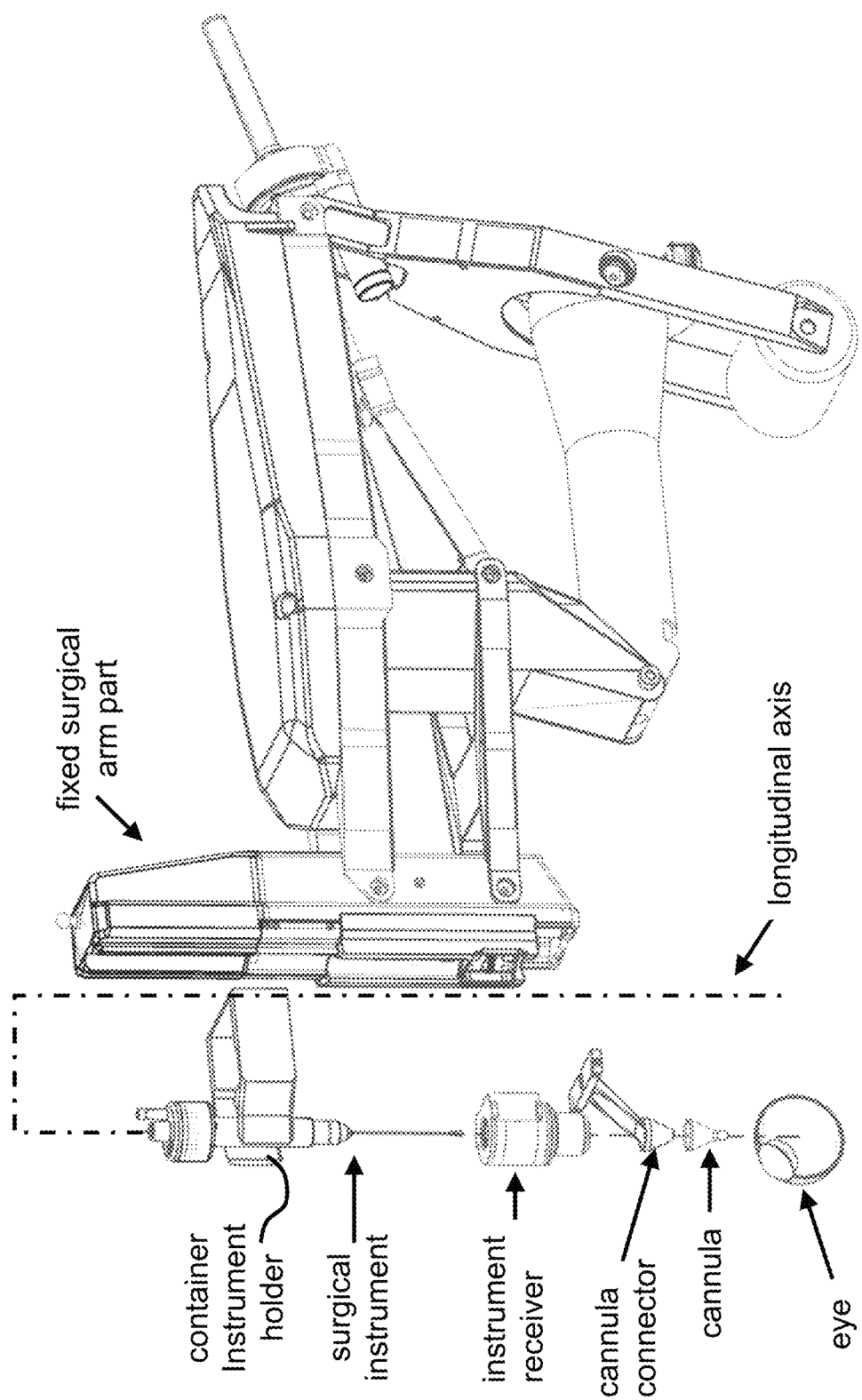

SURGICAL ROBOT

CROSS-REFERENCE TO RELATED APPLICATIONS

This application is a divisional/continuation/continuation-in-part of U.S. patent application Ser. No. 13/971,300 filed Aug. 20, 2013, which is incorporated herein by reference.

U.S. patent application Ser. No. 13/971,300 filed Aug. 20, 2013 is a continuation-in-part of U.S. patent application Ser. No. 12/301,158 filed Dec. 31, 2008 (U.S. Pat. No. 8,512,353 issued Aug. 20, 2013), which is incorporated herein by reference. U.S. patent application Ser. No. 12/301,158 filed Dec. 31, 2008 is a 371 of PCT Patent Application PCT/NL2007/000117 filed May 4, 2007, which claims the benefit of NL Application 1031827 filed May 17, 2006.

U.S. patent application Ser. No. 13/971,300 filed Aug. 20, 2013 is a continuation-in-part of U.S. patent application Ser. No. 13/499,374 filed Mar. 30, 2012, which is incorporated herein by reference. U.S. patent application Ser. No. 13/499,374 filed Mar. 30, 2012 is a 371 of PCT Patent Application PCT/NL2010/050641 filed Oct. 1, 2010, which claims the benefit of NL Application 1037348 filed Oct. 2, 2009.

FIELD OF THE INVENTION

The invention relates to surgical robots. In particular, the invention relates to surgical robots for minimally invasive surgery.

BACKGROUND OF THE INVENTION

In recent years surgical robotic systems have become a significant aid in surgical procedures. Robotic-assisted surgery is intended to overcome certain limitations of minimally invasive surgery and to enhance the capabilities of surgeons performing surgery.

In the case of robotic-assisted minimally invasive surgery, instead of directly moving the instruments, the surgeon could use e.g. either a direct telemanipulator or through computer control to control the instruments. A telemanipulator is a remote manipulator that allows the surgeon to perform the normal movements associated with the surgery while the robotic arms carry out those movements using surgical instruments and manipulators to perform the actual surgery on the patient. In a computer-controlled system the surgeon could use a computer to control the robotic arms and its end-effectors, though these systems could also still use telemanipulators for their input.

The present invention advances the art of surgical robots for minimally invasive surgeries.

SUMMARY OF THE INVENTION

The present invention provides a surgical robot for performing minimally invasive surgery (e.g. in the eye). The surgical robot is movably attached to a surgical operating table via a base element. A surgical arm has a fixed and movable arm part, whereby the movable part is movable with respect to the fixed part. A surgical instrument can be mounted at the movable part. A cannula connection is positioned at the fixed part and aligned with the movable part for allowing the surgical instrument that is mounted to the movable part to pass through the cannula connection. One or more reference arms and manipulation arms connect the base element with the fixed part of the surgical arm. In one example, the base element could have a surgical operating table attachment part and rotating parts movably attached to the surgical operating table attachment part.

BRIEF DESCRIPTION OF THE DRAWINGS

FIG. 4 shows the instrument manipulator similar to FIGS. 1-3 with the container instrument holder, the surgical instrument, instrument receiver, cannula connector and cannula.

DETAILED DESCRIPTION

Figure 1:
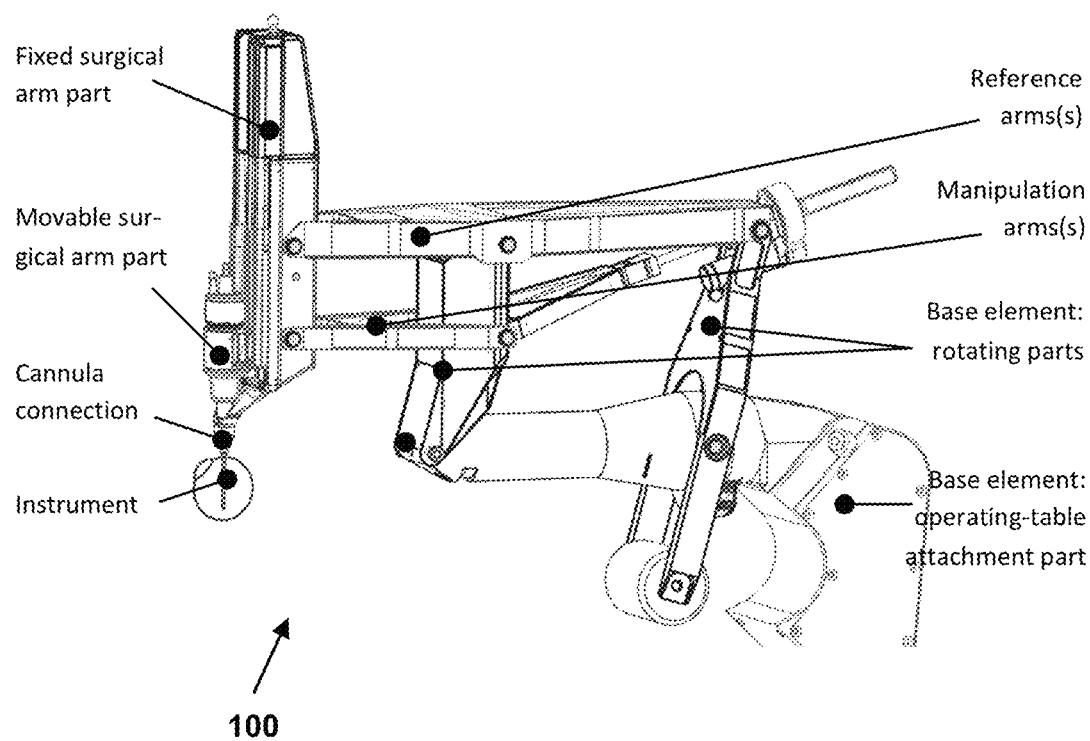
FIG. 1 shows a three-dimensional view of a robotic instrument manipulator 100 according to an exemplary embodiment of the invention.
Figure 2:
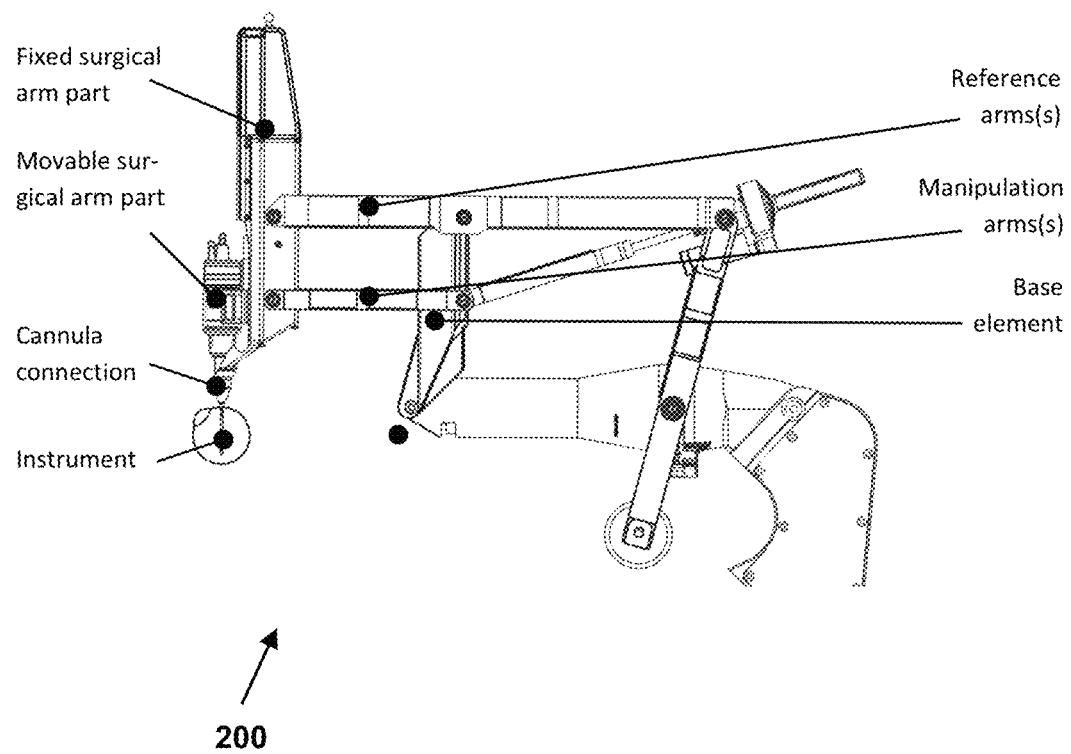
FIG. 2 shows a side-view of a robotic instrument manipulator 200 according to an exemplary embodiment of the invention.
Figure 3:
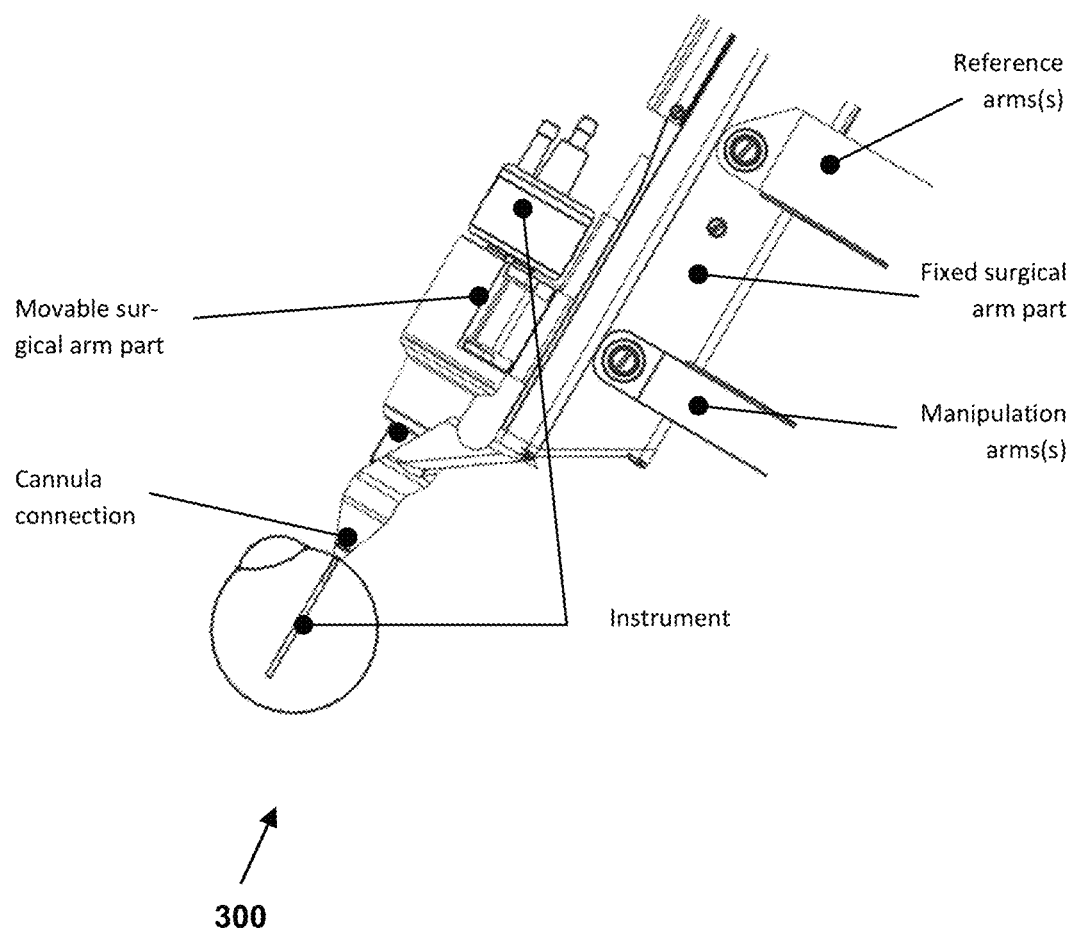
FIG. 3 shows a close-up view 300 (compared to views 100 and 200 in FIGS. 1-2) of a surgical arm according to an exemplary embodiment of the invention. An example of an eye is shown at the bottom left of the figure with part of the instrument inside the eye.

FIGS. 1-3 show various views and structural components of a surgical robot intended for performing minimally invasive surgery. A surgical arm is shown with a fixed surgical arm part and a movable surgical arm part. The movable surgical arm part is movable with respect to the fixed surgical arm part. The fixed surgical arm part has a first engagement point and a second engagement point.

A surgical instrument is mounted at the movable arm part. A cannula connection is positioned at the fixed surgical arm part, which is aligned with the movable surgical arm part for allowing the surgical instrument that is mounted to the movable surgical arm part to pass through the cannula connection. The cannula connection can be affixed onto a cannula on a human or an animal body (e.g. an eye as shown in FIGS. 1-3).

A reference arm is pivotally engaged with the first engagement point of the fixed surgical arm part using one end of the reference arm. The reference arm is further pivotally engaged with a base element using the other end of the reference arm.

In another example, the reference arm has two reference arms (e.g. FIG. 1). One end of both references arms pivotally engages with the first engagement point of the fixed surgical arm part, whereas the other end of both reference arms pivotally engages with the base element. The connection with the base element could be a common attachment point. In yet another example, the two reference arms define a V-shape such that the V-shape diverges in the direction towards the base element. In still another embodiment, the length of the reference arm(s) could be adjusted by activating a drive means.

A manipulation arm is pivotally engaged with the second engagement point of the fixed surgical arm part using one end of the manipulation arm. The manipulation arm is further pivotally engaged with the base element using the other end of the manipulation arm.

In another example, the manipulation arm has two manipulation arms (e.g. FIG. 1). One end of both manipulation arms pivotally engages with the second engagement point of the fixed surgical arm part, whereas the other end of both manipulation arms pivotally engages with the base element. The connection with the base element could be a common attachment point. In yet another example, the two manipulation arms define a V-shape such that the V-shape diverges in the direction towards the base element. A manipulation control and driving means could be used for controlling the manipulation arm(s).

The base element is preferably (movably) attached to a surgical operating table. In one example, as depicted in FIGS. 1-2, the base element distinguishes an operating-table attachment part, which could be movably attached to a surgical operating table. In this example the base element further distinguishes rotating parts movably attached to the operating-table attachment part to control the position the surgical arm of the robot over the surgical area.

FIG. 4 shows in an exploded view, for clarity, the container instrument holder, the surgical instrument, instrument receiver, cannula connector and cannula. The manipulator front end has a fixed surgical arm part defining a longitudinal axis with a proximal end and a distal end. A container is movably connected to the base body near the proximal end of the longitudinal axis. The container has a container instrument holder for holding a surgical instrument. The container instrument holder has a through-hole for holding the surgical instrument. The through-hole has a proximal end and a distal end in the direction of the longitudinal axis. At least part of the surgical instrument when held in the container instrument holder extends past the distal end of the through-hole and towards the distal end of the base body. An instrument receiver receives the surgical instrument from below the distal end of the respective through-hole of the instrument holder. The instrument receiver could have a clamping mechanism to clamp the surgical instrument when the clamping mechanism is changing from a passive no-clamping state to an active clamping state. A cannula connector with a proximal end and a distal end both is aligned parallel with the longitudinal axis of the base body. The cannula connector is a rigid connector mounted to the distal end of the base body. The surgical instrument goes through the cannula connector. The cannula connector remains distal to the instrument receiver and is parallel with the longitudinal axis of the instrument receiver. The cannula connector can be fixated onto a cannula to establish a connection between the base body and the cannula via the cannula connector such that the cannula is also aligned with the longitudinal axis. A linear guide is used to actively guide the instrument receiver towards the instrument holder such that the instrument receiver can actively clamp the surgical instrument through the clamping mechanism. The linear guide can actively guide the instrument receiver with the clamped surgical instrument in longitudinal direction towards the cannula connector. The translation of the instrument receiver towards the cannula connector, while the surgical instrument is clamped by the clamping mechanism of the instrument receiver, causes the surgical instrument to be released from the instrument holder.

Further details, other embodiments and/or examples are described in U.S. patent application Ser. No. 12/301,158 filed Dec. 31, 2008 (U.S. Pat. No. 8,512,353 issued Aug. 20, 2013) and U.S. patent application Ser. No. 13/499,374 filed Mar. 30, 2012, both of which are incorporated herein by reference for all that they teach.

What is claimed is:

1. A surgical robot for performing minimally invasive surgery, comprising:
   (a) a base element;
   (b) a surgical arm, wherein said surgical arm has a fixed surgical arm part fixed to said base element and a movable surgical arm part which is movable with respect to said fixed surgical arm part, wherein said fixed surgical arm part has a first engagement point and a second engagement point, wherein the fixed surgical arm part has a guide connected to the fixed surgical arm part wherein the guide defines a longitudinal axis and a path along which the movable surgical arm part engages and travels along the guide;
   (c) a surgical instrument mounted at said movable arm part;
   (d) a reference arm, wherein one end of said reference arm pivotally connects with said first engagement point of said fixed surgical arm part and wherein another end of said reference arm pivotally connects with said base element;
   (e) a manipulation arm, wherein one end of said manipulation arm pivotally connects with said second engagement point of said fixed surgical arm part and wherein another end of said manipulation arm pivotally connects with said base element;
   (f) a cannula having a conical shape; and
   (g) a cannula connector having a conical shape, wherein the cannula connector is affixed to and near one end of said fixed surgical arm part, wherein said conical shape of said cannula connector is adapted to fit and align inside the conical shape of said cannula, and wherein said cannula connector with fitted cannula are aligned with said movable surgical arm part for allowing said mounted surgical instrument to pass through said cannula connector and said cannula.

2. The surgical robot as set forth in claim 1, wherein said base element is affixed to a surgical operating table.

3. The surgical robot as set h in claim 1, wherein said base element comprises a surgical operating table attachment part and rotating parts attached to said surgical operating table attachment part.

4. The surgical robot as set forth in claim 1, wherein said cannula could be positioned within a human or an animal body.

5. The surgical robot as set claim 4, wherein said human or animal body is an eye.

6. The surgical robot as set forth in claim 1, wherein said surgical robot is part of a master-slave operating system.

7. The surgical robot as set forth in claim 1, wherein manipulation control comprises a computer control system configured to control at least a part of the manipulation arm.

* * * * *